United States Patent [19]

Mersch et al.

[11] Patent Number: 5,030,207

[45] Date of Patent: Jul. 9, 1991

[54] INSTANTANEOUS VEIN ENTRY INDICATOR FOR INTRAVENOUS NEEDLE

[75] Inventors: Steven H. Mersch, Germantown; David E. Spielvogel, Springboro; Richard W. Beck, Centerville, all of Ohio

[73] Assignee: Becton, Dickinson and Company, Franklin Lakes, N.J.

[21] Appl. No.: 608,495

[22] Filed: Nov. 2, 1990

[51] Int. Cl.$^5$ .............................................. A61M 5/178
[52] U.S. Cl. ..................................... 604/168; 604/900
[58] Field of Search ............... 604/900, 116, 264, 168, 604/272; 128/763, 764, 765, 638, 6

[56] References Cited

U.S. PATENT DOCUMENTS

| | | | |
|---|---|---|---|
| 3,734,095 | 5/1973 | Santomieri | 604/900 X |
| 3,859,998 | 1/1975 | Thomas et al. | 604/900 X |
| 4,971,068 | 11/1990 | Sahi | 128/763 |

*Primary Examiner*—John D. Yasko
*Attorney, Agent, or Firm*—Robert P. Grindle

[57] ABSTRACT

A device is provided for indicating when an intravenous needle has entered the vein through the use of a solid fiber optic mounted in the needle for showing visual instantaneous vein entry. The distal end of the fiber optic is polished to be flush with the distal point of the needle. The fiber optic is sized to have an outer diameter which will extend through the cannula of the needle. This polished distal end reflects color, such as red blood, immediately upon vein entry and exposure to blood to the magnifying system forming a part of the invention at the rear or proximal end of the fiber optic. The user observes immediate vein entry without any blood flow or exposure to blood. Other embodiments utilize the fiber optic as the needle, thus eliminating the needle itself.

7 Claims, 2 Drawing Sheets

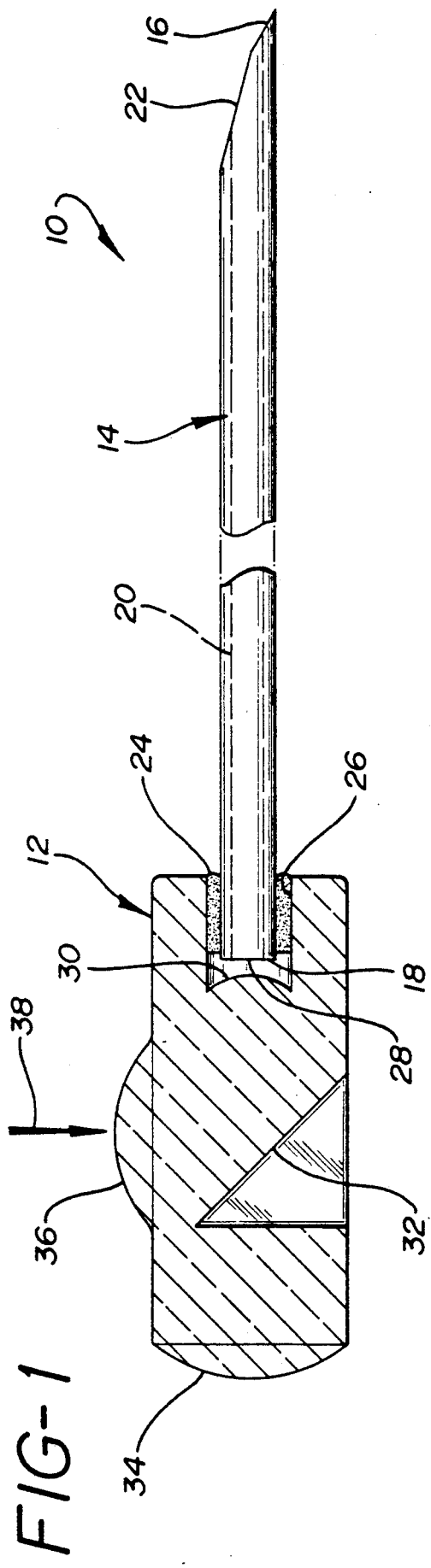
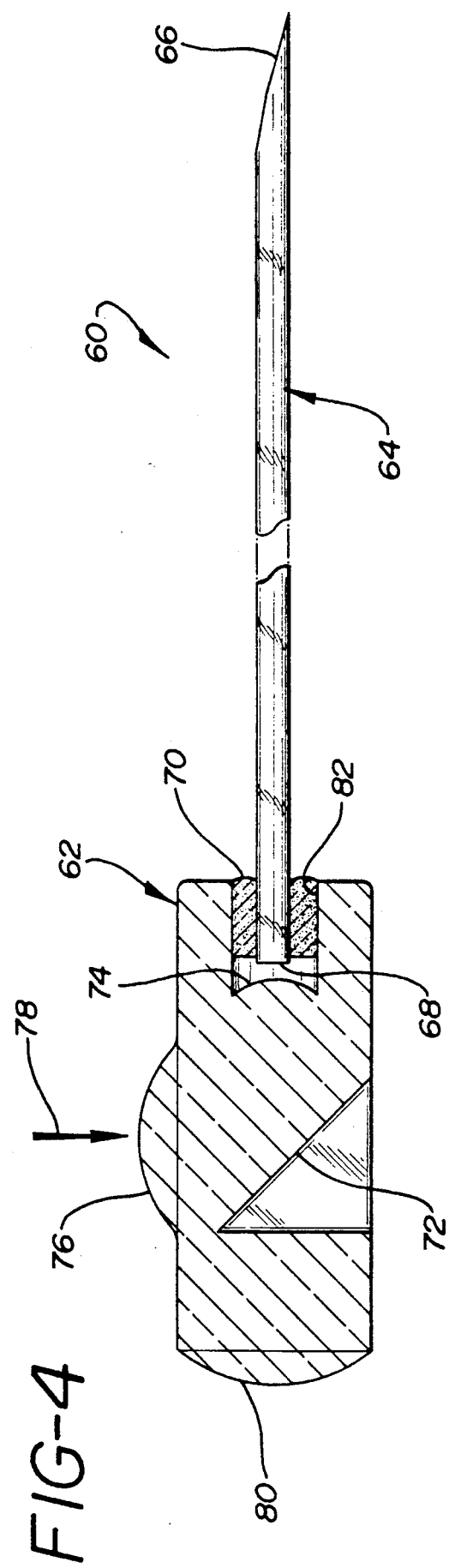

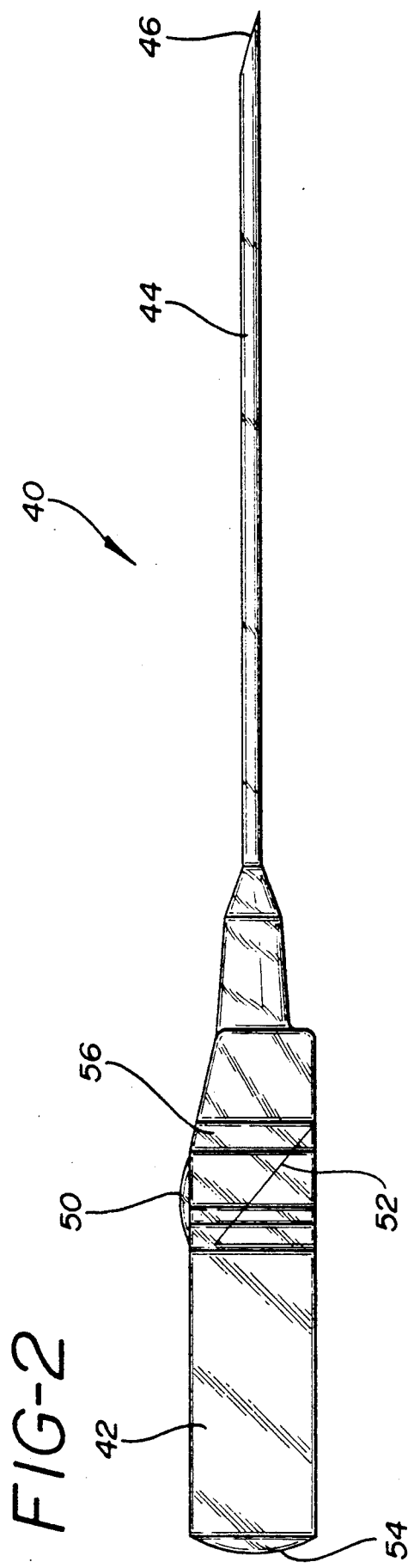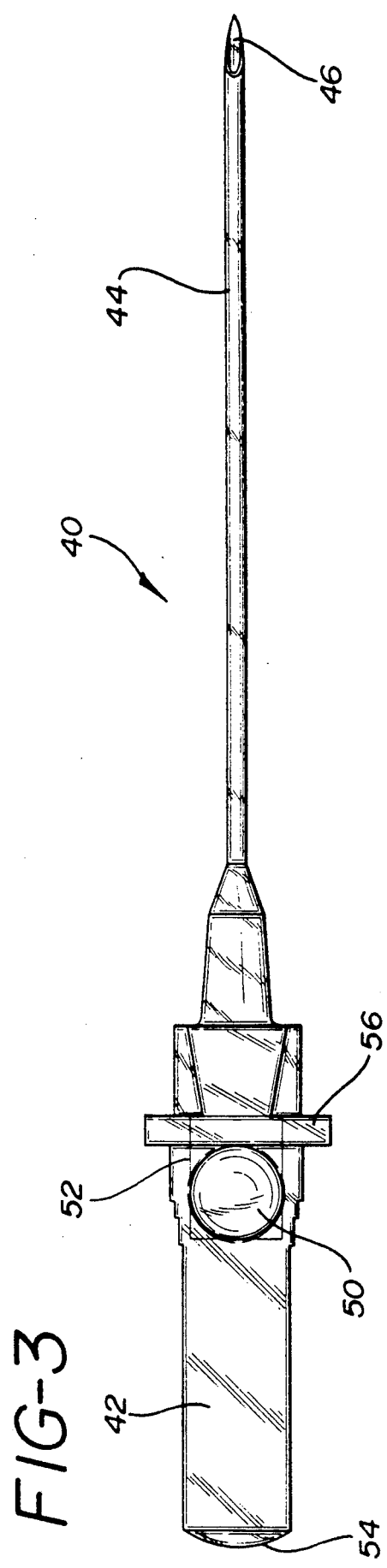

INSTANTANEOUS VEIN ENTRY INDICATOR FOR INTRAVENOUS NEEDLE

BACKGROUND AND STATEMENT OF THE INVENTION

When a clinician or other person in the medical field wishes to insert a needle into the vein of a patient for subsequent application of medication, or for other reasons, it is important that that person know when vein entry has been made. That is, the needle is inserted through the skin of the patient and the point of the needle proceeds inwardly until one side wall of the vein has been punctured. It is at this point that the technician or other person making the vein entry understand that the vein entry has actually been made so that the injection or other anticipated procedure can then follow.

Because the introduction of the assembly into the vein is normally accomplished by the use of a rigid metallic needle, it is impossible to detect the presence of blood in the needle and needle hub and, likewise, the presence of the needle tip in the vein. For example, introducer needles are normally equipped with a hub at the proximal end thereof, and some devices have equipped the hub portion of the needle with a transparent flash chamber into which the blood may flow in order to indicate to the user that the needle point is properly placed. However, in order to induce blood flow from the needle point to the flash chamber venting of air therefrom is required, and the flow of blood from the flash chamber was controlled by a plug that was inserted into the chamber after the blood had actually appeared therein. As a consequence, if the plug was not placed at the proper time, blood would flow from the chamber through the air vent and leak over the person using the instrument.

One approach to this undesirable effect of having the user of a device become contaminated with blood flowing during the time that they were attempting to indicate whether there was vein entry, arrangements have been made to provide a blood-detecting chamber at the proximal end of the device with the chamber being provided with a convenient means for venting air from the needle cannula. As the blood flows from the vein toward the proximal end of the device, the vent will expel air and allow for the blood detecting chamber to be filled with blood so that the user knows that vein entry has been made, but still provide a venting action which would not allow the blood to flow through the vent.

Many arrangements have been made of configurations of vents in order to prevent actual blood flow through the vents, while still providing the proper venting of the air from the chamber or cannula of the needle so that blood will actually be induced to flow from the vein of the patient to the proximal end of the device where the blood detecting chamber is located. One such device is described and claimed in U.S. Pat. No. 3,859,998 which utilizes a breather slit in the "flashback" chamber at the proximal end of the device. The slit allows for the air to pass so the blood will flow to the flashback chamber which is a transparent walled chamber so that blood can be viewed therein. The slit is of a dimension which prevents blood from flowing from the flashback chamber onto the user of the device.

However, such slits are not always completely satisfactory and blood leakage does take place. Aside from this, there is an amount of time taken from the time of vein entry until the time that the blood flows to the flashback chamber. During this procedure, the user may have inserted the point at the distal end of the cannula inwardly too far and passed entirely through the vein to the opposite wall thereof so that there is not, in fact, vein entry for the subsequent application of the use of the instrument, as desired.

Other arrangements for enhancing the use of a flashback chamber include the invention described and claimed in European Patent Publication No. 0139872 which shows a flashback chamber with a magnifier 13. This has the effect of increasing the visual appearance of blood in a transparent flashback chamber, so that the user may more quickly realize that vein entry has been made.

A further structure designed to indicate that vein entry has been made, utilizing a flashbacktype chamber for visual observation of the presence of the flow of blood is taught and claimed in U.S. Pat. No. 4,365,630, which teaches a transparent maze-type arrangement for indicating to the user the presence of blood and the fact that vein entry has been realized. While this reduces the time from vein entry until a visual indication thereof, there is still a time interval which may cause difficulties, as discussed above.

With this invention, by contrast, a new arrangement is provided in which the user realizes instantaneously when vein entry has been made. That is, no blood flow is required to a flashback chamber and, indeed, no flashback chamber is present. The invention here utilizes a fiber optic which extends through an intravenous needle, for example. The front end of the fiber optic is flush with the distal end of the introducer needle. The front end, in turn, of the fiber optic is ground so that it is indeed flush with the needle point as it is inserted through the wall of the vein of a patient.

The fiber optic is an elongated device with an outer diameter of a size which will fit through the internal diameter of the lumen of the needle involved. The fiber optic extends to the proximal end of the needle to a one-piece solid magnifying assembly which projects the indication passing visually through the fiber optic from the polished front or distal end of the fiber optic to indicate instantaneously vein entry.

That is, a magnifying arrangement provides optical illumination of the actual vein entry so that no blood is required to flow through the introducer needle to the rear end thereof prior to such time that vein entry is realized. The user will know simply by looking at the magnifying surface that the dark red color of venous blood is present at the distal end of the needle and the fiber optic.

In order for the observer to observe vein entry, there must be sufficient light at the distal end of the needle and fiber optic. This is realized in a number of ways. First, for situations where the skin is fairly thin and translucent (for example in neonates, babies and elderly) ordinary good ambient lighting is sufficient. In situations where the skin is thicker, darker or dark pigmented, it is necessary to have supplemental lighting. This is accomplished using any light source which externally illuminates the area where vein entry is to take place.

One particular device that works particularly well for this situation is the Landry Vein Light TM, a product of Applied Biotech Products, Inc., Scott, LA 70583, which illuminates peripheral veins for intravenous therapy. A further approach is to concentrate supplemental lighting through the proximal end of the fiber optic with lenses molded into the plastic hub in accordance herewith.

With this arrangement, therefore, no venting is required. No blood flow is required. The arrangement is bloodless so there is no fear of contamination by the user of the blood of the patients involved. Moreover, because the fiber optic can be made of any dimension, it works for all gauges of needles, even such small gauge needles as 30 gauge. There is constant monitoring of the needle tip with, as indicated above, instant indication of vein entry and/or any other conditions present at the distal end of the needle, for that matter.

Other objects and advantages of this invention will be apparent from the following description, the accompanying drawings and the appended claims.

DESCRIPTION OF THE DRAWING

FIG. 1 is a side elevational view of the device of the invention as mounted on an insertion needle;

FIG. 2 is a side elevational view of a further embodiment of the invention in the form of a single integral fiber optic needle and hub;

FIG. 3 is a top plan view of the embodiment shown in FIG. 2; and

FIG. 4 is a side elevational view of yet a further embodiment of the invention similar to that of FIG. 1 without a separate needle, and utilizing the fiber optic as the needle.

DETAILED DESCRIPTION OF THE INVENTION

Referring to the drawings, FIG. 1 shows the needle insertion assembly of the invention generally designated 10, and including a clear proximal body portion 12 in the form of a solid clear transparent material, which may be a molded glass or plastic material. Other representative materials include polystyrene, liquid crystal, polyacrylates, polycarbonate and blends thereof. The head includes an annular front end opening 26 which receives the needle assembly 14 therein. That is, the proximal end 18 of needle 14 is held in place in opening 26 by an adhesive or glue material such as an epoxy 24.

Mounted in needle 14 is a fiber optic 20. As can be seen in FIG. 1, the distal end 22 of fiber optic 20 has been polished to conform to the configuration of the pointed needle end 16 of needle 14 for ready insertion of the assembly through the skin and through the wall of a vein of the patient.

Surfaces 30 and 36 formed on the solid body 12 serve as lenses which form a magnifying system to magnify surface 28 for the observer or user or operator of the device indicated diagramatically at 38. Surface 32 acts as a mirror by providing total internal reflection for the rays traveling from 30 to 36. Surfaces 30 and 34 provide a means of focusing supplemental ambient light to the surface 28, as discussed above. The fiber optic will then transmit the supplemental light to the needle point 22.

At this point, the light interacts with its environment and a portion of it will be reflected or scattered back down the fiber optic 20 to the surface 28. When vein entry has been made, the observer will view a magnified image of surface 28, and therefore is viewing the environmental conditions at the needle point 16, 22. Obviously, the user may distinguish between the color of tissue tinted with bright red capillary blood as the distal end 16, 22 passes through the skin of a patient until such time as vein entry has been made. Then the observer will view the color of dark red venous blood for accurate indication of the position of the needle tip.

It should be borne in mind that at this point in time, the user has an indication of vein entry and no waiting period is required for blood to flow back through the needle to a flashback chamber. No arrangement is required to allow the venting of air from a flashback chamber. All of this is eliminated because of the instantaneous observation of vein entry with the invention here.

Thus, as will be appreciated from the above, there is provided in accordance with this invention, a provision for instantaneous vein entry indication for the users of the device of the invention. Moreover, the insertion assembly of the invention is relatively inexpensive and uncomplicated in its construction, but, nevertheless, provides a structure for imparting a precise indication of vein entry immediately when that occurrence takes place. No further manipulation is required in order to find out precisely whether or not vein entry has been made or waiting for blood to move over a period of time to a flashback chamber.

Moreover, with the invention here, small gauge needles, which do not ordinarily allow rapid flow of blood to the needle hub viewing area of prior art devices may be easily used. The design here provides immediate information for all gauge needles. The arrangement of the invention enables the viewer to observe the color environment at the sensing tip at all times.

While this invention, as described above, envisions a separate metal intravenous needle with a fiber optic extending therethrough as described above, it is within the purview of this invention to use the fiber optic itself as the introducer needle. In such circumstances, as will be understood by practitioners-in-the-art, the distal end of the fiber optic is polished to provide an insertion point. It will be understood by practitioners-in-the-art that an I.V. catheter placed over the fiber limits the sensing area to the polished distal end or tip of the fiber optic, which, during use, extends beyond the distal end of the catheter. The proximal end of the fiber optic, in such circumstances is, itself, mounted in the bore on the distal surface of the instrument hub, as described above.

Such an embodiment is shown in FIG. 4 wherein the arrangement 60 is shown with a hub 62 having a distal bore or front end opening 82 for receiving the proximal end 68 of fiber optic 64. With such an arrangement, a transparent adhesive 70 is utilized. With this embodiment, as with the embodiment in FIG. 1, surfaces 74 and 76 formed on hub body 62 serve as lenses, which form a magnifying system to magnify surface 68 for the user 78. Surface 72 acts as a mirror providing total internal reflection for the rays traveling from 74 to 76. Surfaces 74 and 80 focus supplemental ambient light to surface 68. Fiber optic 64 will then transmit this supplemental light to needle point 66.

Referring now to FIGS. 2 and a further embodiment 40 is shown in the form of a single integral instrument with hub 42 and fiber optic 44 molded as a single piece. Such an arrangement is particularly important from a cost effective standpoint since only a single molding procedure is required.

In this arrangement, mirror 52 directs light rays directly from distal end 46 of fiber optic 44 through magnifying lens 50. The focal length of lens 50 is set to present a magnified image of distal end 46 to the user, through mirror 52. Again, surface 54 serve to focus supplemental ambient light to distal end 46. With this arrangement, a material may be selected which is particularly appropriate for grinding distal end 46 to a point for ready insertion into a patient.

While the form of apparatus herein described constitutes a preferred embodiment of the invention, it is to be understood that the invention is not limited to this precise form of apparatus, and that changes may be made therein without departing from the scope of the invention which is defined in the appended claims. For example, whereas one form of magnifying arrangement is shown, it will be understood that various configurations of magnifying arrangements can be provided for directing the flow of light to the distal end of the device as well as arrangements for magnifying the resulting reflection of the conditions at the distal end of the fiber optic and/or needle point to the observer at the proximal end.

What is claimed is:

1. An instantaneous vein entry indicator system for needles, comprising
   (a) a needle;
   (b) said needle extending from a pointed distal end to a proximal end;
   (c) a lumen in said needle extending from said pointed distal end to said proximal end;
   (d) a fiber optic mounted in said needle lumen and extending from said pointed distal end to said proximal end;
   (e) a solid single piece transparent needle hub having a distal end and a proximal end;
   (f) a bore positioned in the distal end of said needle hub for fixedly receiving the proximal end of said needle and said fiber optic;
   (g) a first magnifying lens positioned on said hub in the base of said bore adjacent and spaced from the fiber optic proximal end;
   (h) a second magnifying lens positioned on said hub at right angles to said first magnifying lens;
   (i) a mirror surface positioned between said first and said second magnifying lenses to transfer total internal reflection for light rays traveling between said first and second magnifying lens; and
   (j) a third magnifying lens positioned on the proximal end of said hub;
   (k) whereby said first and third magnifying lenses focus ambient light on the proximal end of said fiber optic for transmitting light to said needle pointed distal end, and said first and second magnifying lenses magnify the image at the proximal end of said fiber optic for the user.

2. The system of claim 1, in which
   (a) the end of said fiber optic adjacent the pointed distal end of said needle is polished to conform to the adjacent pointed surface of said needle pointed distal end.

3. The system of claim 1, in which
   (a) said fiber optic and said needle hub are comprised of a material selected from the group consisting of glass, polystyrene, liquid crystal, polyacrylate, polycarbonate, and mixtures thereof.

4. An instantaneous vein entry indicator for intravenous needles, comprising
   (a) an elongated fiber optic having a distal end and a proximal end;
   (b) said distal end of said fiber optic being ground and polished to a point for insertion through the skin;
   (c) a solid single piece transparent hub having a distal end and a proximal end;
   (d) a bore positioned in the said distal end of said hub for fixedly receiving the proximal end of said fiber optic;
   (e) a first magnifying lens positioned on said hub in the base of said bore adjacent and spaced from the said fiber optic proximal end;
   (f) a second magnifying lens positioned on said hub at right angles to said first magnifying lens;
   (g) a mirror surface positioned between said first and said second magnifying lenses to transfer total internal reflection for light rays traveling between said first and said second magnifying lens;
   (h) a third magnifying lens positioned on the proximal end of said hub;
   (i) whereby said first and third magnifying lenses focus ambient light on the proximal end of said fiber optic for transmitting light to said fiber optic pointed distal end, and said first and second magnifying lenses magnify the image at the proximal end of said fiber optic for the user.

5. The indicator of claim 4, in which
   (a) said fiber optic and said needle hub are comprised of a material selected from the group consisting of glass, liquid crystal, polystyrene, polyacrylate, polycarbonate and mixtures thereof.

6. An instantaneous vein entry indicator for intravenous needles, comprising
   (a) an elongated solid, round fiber optic having a pointed distal end;
   (b) a hub positioned and integral with said fiber optic at the end of said fiber optic opposite said pointed distal end;
   (c) said integral fiber optic and said hub being transparent;
   (d) a first magnifying lens positioned on said hub perpendicular to the axis of said fiber optic;
   (e) a mirror surface positioned in said hub between said first magnifying surface and the axis of said fiber optic; and
   (f) a second magnifying lens positioned on the proximal end of said hub:
   (g) whereby said second magnifying lens focuses ambient light on the proximal end of said fiber optic for transmitting light to said fiber optic pointed distal end, and said first magnifying lens magnifies the image at the proximal end of said fiber optic for the user.

7. The indicator of claim 6, in which
   (a) said fiber optic and said needle hub are comprised of a material selected from the group consisting of glass, liquid crystal, polystyrene, polyacrylate, polycarbonate and mixtures thereof.

* * * * *